United States Patent
DeLegge et al.

(12) 
(10) Patent No.: US 6,471,676 B1
(45) Date of Patent: Oct. 29, 2002

(54) CATHETER AND FEEDING TUBE RETENTION DEVICE AND METHOD OF USE

(75) Inventors: Rebecca DeLegge, Mount Pleasant, SC (US); Lester David Michels, Eden Prairie, MN (US); Kathleen Stauter, Lino Lakes, MN (US)

(73) Assignee: Novartis Nutrition AG, Berne (CH)

( * ) Notice: Subject to any disclaimer, the term of this patent is extended or adjusted under 35 U.S.C. 154(b) by 0 days.

(21) Appl. No.: 09/532,380

(22) Filed: Mar. 21, 2000

(51) Int. Cl.[7] .............................................. A61M 5/32
(52) U.S. Cl. ..................................................... 604/175
(58) Field of Search .................................. 604/174, 175, 604/176, 19, 48, 93.61; 128/760; 206/364

(56) References Cited

U.S. PATENT DOCUMENTS

| | | | |
|---|---|---|---|
| 4,834,712 A | 5/1989 | Quinn et al. ................. | 604/175 |
| 5,078,703 A | 1/1992 | Bryant ......................... | 604/283 |
| 5,267,969 A | 12/1993 | Hirsch et al. ............... | 604/174 |
| 5,318,543 A | 6/1994 | Ross et al. ................... | 604/164 |
| 5,374,254 A | 12/1994 | Buma .......................... | 604/175 |
| 5,451,212 A | 9/1995 | Andersen .................... | 604/174 |
| 5,549,657 A | 8/1996 | Stern et al. .................. | 604/283 |
| 5,658,267 A * | 8/1997 | Colacello et al. ........... | 604/327 |
| 5,807,341 A * | 9/1998 | Heim .......................... | 604/174 |
| 5,848,989 A * | 12/1998 | Villani ......................... | 604/93 |
| 5,860,960 A | 1/1999 | Quinn ......................... | 604/178 |
| 5,865,816 A | 2/1999 | Quinn ......................... | 604/280 |
| 5,879,330 A * | 3/1999 | Bell ............................ | 604/175 |
| 5,882,341 A * | 3/1999 | Bousquet ............. | 128/DIG. 26 |
| 6,022,335 A * | 2/2000 | Ramadan .................... | 604/175 |
| 6,197,004 B1 * | 3/2001 | Nicolosi ............. | 128/DIG. 26 |
| 6,228,063 B1 * | 5/2001 | Aboul-Hosn ................ | 604/174 |
| 6,319,231 B1 * | 11/2001 | Andrulitis ................... | 604/175 |

FOREIGN PATENT DOCUMENTS

EP    0 865 799    9/1998    .......... A61M/25/02

* cited by examiner

Primary Examiner—Teresa Walberg
Assistant Examiner—Daniel Robinson
(74) Attorney, Agent, or Firm—John W. Kung

(57) ABSTRACT

A catheter retention device comprises an oval base with a centrally located bore there through, an elevated disk portion surrounding said bore and two retention ring housing elements with centrally disposed bores whose axis are perpendicular to one another. The retention device is useful in securing the catheter so that any inadvertent physical force or traction exerted against it will not move the catheter or pull it from its incision. The catheter itself is threadably inserted through all the bores of the retention device which is then attached to the patients body at the ostomy site with sutures, tape or liquid adhesives. Preferably, the retention device is used in conjunction with gastrostomy or jejunal feeding tubes.

19 Claims, 4 Drawing Sheets

A.

CATHETER AND FEEDING TUBE RETENTION DEVICE AND METHOD OF USE

FIELD OF THE INVENTION

The invention relates generally to catheters placed in patients in need of same, and more specifically, to feeding tubes surgically implanted in patients who for one reason or another, cannot receive their daily nutritional intake orally. More particularly, the invention relates to gastrostomy and jejunal feeding tubes and means for their attachment to the patient.

BACKGROUND OF THE INVENTION

There are many patients affected with disease, stroke or other physiological conditions that result in the inability to normally receive nutrition through the mouth which is then swallowed and broken down and absorbed by the digestive system. People suffering from stroke, Alzheimer's disease, cancer, inflammation or other infirmities often cannot properly chew or swallow their food or medication which must then be delivered to the patient in another fashion if starvation and malnutrition are to be avoided.

Gastroenterologic feeding tubes have been known for years and are inserted into the stomach by any one of a number of different methods. Generally, a catheter is placed in the body by way of the mouth and is either pulled or pushed downward into the stomach and either left there or is pushed further down into the jejunum of the small intestine. The feeding tubes may also enter the body either by way of the nasal passageway or by means of a gastrostomy in which they are surgically implanted through the abdomen.

The present invention relates to the enteral feeding of patients by these tubes and more particularly to a gastrostomy or jejunal feeding tube which is receivable through the wall of the stomach for feeding and medicating a patient and/or for draining fluids from the patient's stomach. The present invention also relates to a jejunostomy tube which similarly is receivable into the small intestine from outside the patient's abdomen.

The use of feeding tubes which extend directly into the stomachs of patients is often required when patients cannot swallow or when they have structures in their esophagi which prevent food from entering their stomachs. In a situation of this type, it is common to perform a gastrostomy on a patient wherein an opening is formed in the skin, facia and stomach wall and wherein a gastrostomy tube is inserted in the opening to allow food, fluid and/or medication to be passed directly into the stomach and also to allow bodily fluids to be drained therefrom.

Various types of gastrostomy devices have been inserted in patients by means of a percutaneous insertion, a surgical placement, a radiological placement or others. The procedures employed generally follow those known as the Sachs-Vine procedure, the Gauderer and Ponsky procedure, and others. Typical patents describing these procedures and publications of the technique are set forth in the U.S. Pat. Nos. 4,861,334 to Nawaz, U.S. Pat. No. 4,900,306 to Quinn et, al. and U.S. Pat No. 5,080,650 to Hirsch et. al. all of which are hereby incorporated by reference.

Enteral feeding tubes that enter the stomach through surgically incised openings through the skin, facia and peritoneum must be secured in some manner so that the tube does not move about within the patient or be displaced if pulled. Generally, enteral or gastrostomy feeding tubes are either surgically inserted through the skin of the abdomen or fed down to the stomach by way of the mouth and pharynx.

Catheters and enteral feeding tubes which enter the body are frequently held in place by both internal and external means. In some cases, the catheter/tube may have an internal retention means such that the end of the catheter is held in place within a body cavity such as the stomach or the bowel. This internal retainer portion may take the form of a disk, dome, multiple flanges or leaves or an inflatable balloon that is attached to the catheter tip. The external means of retention are often affixed (e.g., adhesives, sutures) to the patient's skin for security from inadvertent traction and removal. Nonetheless, catheters are often inadvertently dislodged by patients or care givers through excessive traction placed on connectors or tubing lines.

Particularly susceptible to inadvertent removal or displacement are those catheters that have no internal retention means and rely only on external attachments or fixation to maintain catheter position. For example, jejunostomy feeding tube which may be placed through the patient's abdomen and into the small bowel frequently consists of only a small bore tube with no expandable or bulbous "tip" present to hold it's position within the lumen of the bowel. Thus, only the external retention means at the patient's skin maintains the tube's position. In some cases, the tube itself, or a retainer or connector attached to the tube, are sutured to the patient's skin. Alternatively, adhesive tape or some other securement or adhesive method might be used. In either of these cases, traction placed on the external connected tubing will apply force directly to the catheter at the point where it enters the body and can result in extraction or displacement of the catheter if the sutures or adhesive releases. Providing a means for shock absorption (aka "strain relief") between the connecting tube and the catheter could reduce the incidence of inadvertent catheter removal or displacement resulting from excessive traction on the tubing.

External retention means and devices also consist of various slidable or lockable components which may be attached to the catheter tube to prevent the tube from migrating inward to the patient. These devices may be sutured or adhered to the patient's skin to reduce the risk that external traction will dislodge the tube. Furthermore, some of these devices provide a single capture ring means for holding the tube in a right angle position from the point where it exits the patient's body. However, none of these external retention means satisfactorily addresses the issue of strain relief in that any traction force will still be transmitted directly to the tubing at the exit site point with the risk of resulting dislodgment.

U.S. Pat. No. 5,865,816 to Quinn, discloses a percutaneous endoscopic gastrostomy tube assembly comprising a distal end retention device which holds the tube in the stomach, secures the catheter and bends it at a right angle to the patient's skin. A bolus tip is comprised of a balloon which, once surgically implanted, is inflated thereby securing the catheter internally to the patient. An external bolster grips the tube at a selected distance from the balloon and forces it at a right angle so that a set connector lies immediately adjacent to the patient's abdomen when in place and is secure thereto.

U.S. Pat. No. 5,860,960 also to Quinn discloses another retention means for securing a gastrostomy tube to the wall of the stomach and the outer skin of the patient as well. The device consists of an elongated body comprised of silicone rubber that is split above a substantial portion of its body to form two legs joined together at one end. The legs are separable at the other end and the enteral feeding tube is inserted therebetween which is then gripped by the legs of the device. This is then turned at a 90° angle to position the feeding tube parallel to the surface of the outer skin affording the patient a more comfortable implantation.

U.S. Pat. No. 5,549,657 to Stem et. al. discloses a low profile adapter for gastrostomy feeding tubes. The adapter comprises an anti-reflux valve assembly having a stem which can be a one—way valve to prevent reflux of the gastric contents but still allows for the administration of dietary supplement to the patient. A clamp is placed around the feeding tube and the valve stem and is locked into place to secure the valve stem to the feeding tube at a location flush with the patients skin. A silicon cover is placed around the clamp to keep the area in a substantially sterile condition.

U.S. Pat. No. 5,374,254 to Buma teaches and claims specialized. catheters which contain adjustable external locking devices to secure the enteral feeding tube so the bolster can rest securely attached to the patient's skins surface. A compression element and engagement elements that attach the tube to the bolster device are located both on the vertically oriented portion of the tubes' curved passageway and the side oriented portion thereof. The bolster device is locked into position by the tension that exists between the engagement elements of the catheter and the side oriented engagement elements of the bolster caused by the denting of the flexible tubular member into the right angle providing a curved passageway within the side port bolster.

U.S. Pat. No. 5,451,212 to Anderson teaches a bumper retention device for securing a catheter or feeding tube at the site of the body opening or ostomy. The retention device maintains the feeding tube in an angular fixation externally against the skin portion connected a loop portion. The loop portion is placed about the outer diameter of the feeding tube and the stem portion is inserted into an end operative of the retention bar so that the feeding tube is secured at a 90° angle.

U.S. Pat. No. 5,318,543 to Ross et. al. discloses a laparoscopic jejunostomy instrumentation kit for the surgical implantation of jejunostomy feeding tubes, one component of which is an external retaining device which is surgically attached to the patient's skin and guides the tube through a 90° bend without kinking the tube. The retaining device is comprised of a base which rests against the patient's skin and is attached thereto and a tube guiding conduit integral thereto which guides the tube 90° in a hole in the base that is aligned with the ostomy. The feeding tube is then fed through the hole and into the stomach.

U.S. Pat. No. 5,267,969 to Hirsch et. al. discloses a similar external retaining device consisting of a base for attachment to the skin and a feeding tube retaining conduit that is integral thereto. The tube enters a first hole in the conduit and is fed through the conduit and then bent at a 90° angle for entry into the ostomy through a second hole in the conduit and base which is aligned and confluent with the ostomy.

PCT/DE98/03285 to Pausch et. al. discloses and claims a device for the fixation of a catheter or ostomy feeding tube comprising a resting plate fitted with a support wall on which the catheter or feeding tube is placed. The support wall guides the catheter or feeding tube at a substantially ninety degree (90°) angle from the surgically incised ostomy away from the patients body. In order to attach and secure the catheter or tube, a pivoting flap folds over the tube and is aligned with the top surface support wall as it is clicked into a closed position. The catheter or tube is thereby folded at the ninety degree (90°) angle without modifying its cross section.

European Patent Application No. EP 0 648 512 B 1 to Van Heasch discloses a flexible bracket for securing a catheter or feeding tube to a patient's body comprising a substantially flat plate that rests against the skin of the patient over the ostomy and a housing that is somewhat cylindrical in shape that receives the catheter tube at one end of the housing from the source of nutrition or medication and then feeds the tube through the ostomy at a substantially ninety degree (90°) right angle. A planar retention means within the stomach or body cavity of the patient secures the catheter or feeding tube from within.

Other examples of catheter and feeding tube retention devices relevant to the present invention may be found in U.S. Pat. No. 5,078,703 to Bryant entitled Catheter Adapter and Retainer; U.S. Pat. No. 4,834,712 to Quinn entitled "Tube Fixation Device" and EPO 865 799 to Balbierz entitled "Adjustable Securing Wings" which discloses and adjustable anchoring device comprised of wings or flanges which retain a catheter at a desired location inside a patient.

None of the above prior art devices effectively provide a means for shock absorption, i.e., strain relief that often occurs between the gastrostomy or jejunal feeding tube and the connecting tubing from the feed part due to the inadvertent pulling or movement of the tube that is external to the patient's body which could result in dislodgment of the tube from the patient with possible dire consequences.

It is an object of the present invention then to provide an improved feeding tube retention device for use outside the patient's body that substantially lowers the risk or eliminates entirely the possible dislodgment of the tube from the ostomy due to the inadvertent pulling or movement of the tube for whatever reason. This will not only prevent the removal or displacement of the tube from the patient's body, but will also prevent or guard against the resultant tearing of sutures and damage to the patient's internal organs, muscular fascia, etc., that may occur.

SUMMARY OF THE INVENTION

The present invention is an external feeding tube retention device comprised of a base with a hole or bore that passes therethrough and multiple retention rings. A first retention ring is located on the base. A second retention ring is located on the base whose axis is out of alignment to that of the first retention ring housing. All three bores, each retention ring providing at least one bore, are substantially equal in circumference and are sized to accommodate the circumference of the feeding tube which is threaded there through resulting in a bending of the tube at a 90° angle from the Y-port connector to the ostomy incision.

DETAILED DESCRIPTION OF THE INVENTION

The feeding tube retention device of the present invention provides protection against feeding tube removal from the patient's body or displacement due to the inadvertent movement of the tube or the unforeseen exertion of external force pulling the tube therefrom. It is particularly useful in conjunction with those tubes that have no internal retention device such as balloons, flanges, domes and the like. The retention device is simple in design and its one-piece construction makes it easier to use than the more complicated, multi-piece retention devices known in the art. The retention device is preferably molded using a flexible material such as silicone rubber or thermoplastic rubber, PVC polyurethene or other plastics or polymers or co-polymers, or mixtures thereof although stiffer, more rigid materials could be employed and the device would still function as intended.

Figure 1:
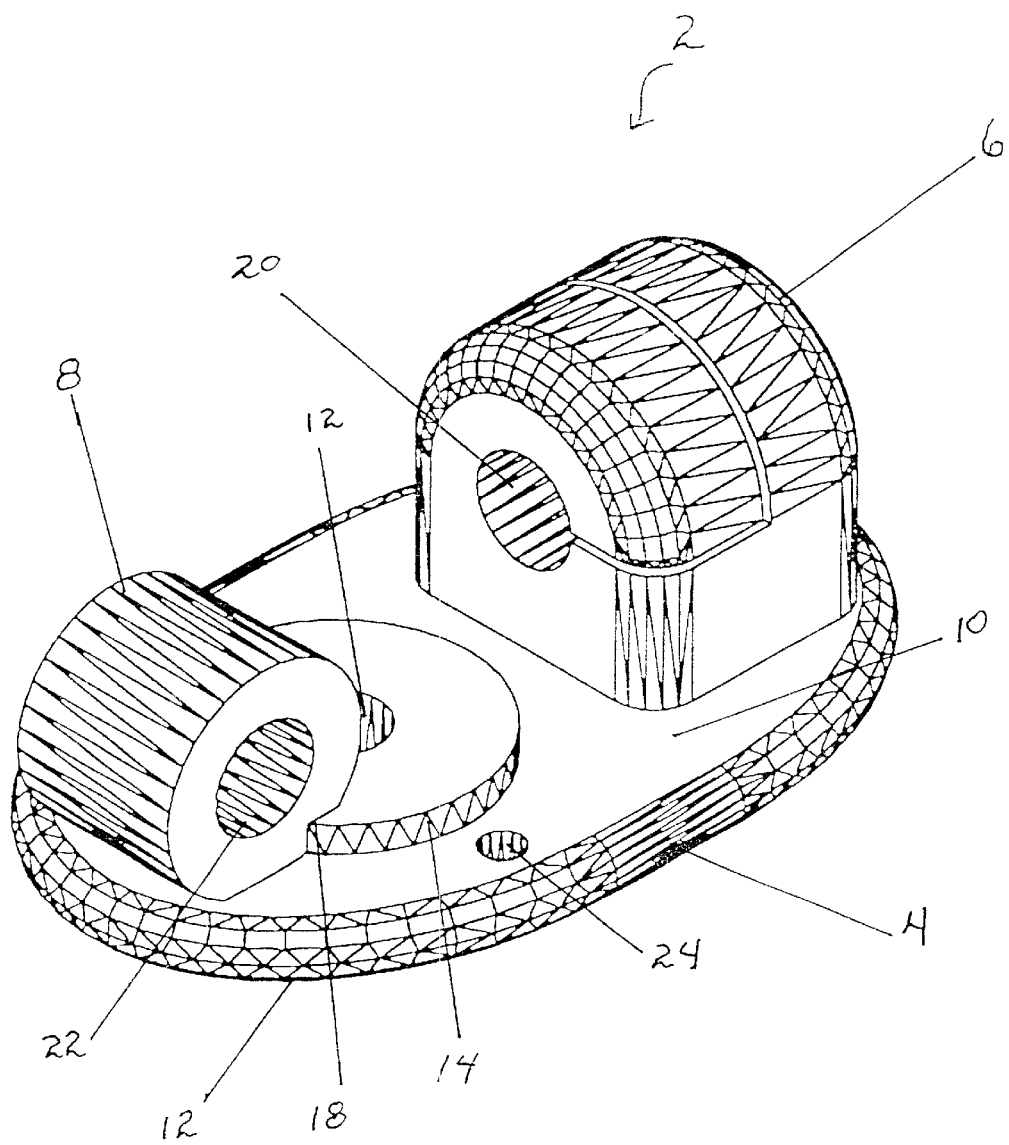
FIG. 1 is an overall schematic view of feeding tube retention device of the present invention.

Referring now to FIG. 1, although integrally constructed as a one piece unit, the retention device (2) is essentially comprised of three basic elements or components. A base component (4) supports a first (6) and second (8) retention units on the top surface of the base (10). Whereas the base (4) is described herein as substantially oval as depicted in the Figures, it is not limited to an oval shape as clearly the base could also be circular, rectangular, square or any other shape provided the components can be functionally accommodated. The thickness of the base may vary but preferably the thickness will be 1.0 cm or less, more preferably in the range of from about 0.1 cm to about 0.5 cm and most preferably from about 0.2 cm to about 0.3 cm.

As evident from FIG. 1, the base portion (4) contains a circular bore (12) that passes through the entire width of the base (4). In a preferred embodiment, an elevated disk shaped element (14) that is substantially circular in shape surrounds said base and is contiguous therewith. The thickness of the elevated disk may vary but generally will be equal to or less than the thickness of the base, e.g., one-third to one-half the thickness of the base. The disk element, when present, increases the surface area of the bore (12) to provide for a better frictional fit for the tube.

FIG. 1 also shows that the circular bore (12) and elevated disk-shaped element of the base (14) are located on the top surface (10) of the base (4), preferably, but not necessarily, off-center in order to physically accommodate the first retention ring housing (6). In fact, the elevated disk element (14) may be tangentially attached along the length of the second retention ring housing (8) in which case a groove (16) may be cut into said housing (8) along its entire length to accommodate the outer edge (18) of the elevated disk element (14).

As further evident from FIG. 1, in a preferred embodiment, the two substantially cylindrical retention ring housing components (6, 8) are separated by the circular bore (12) and each contain centrally disposed bores or channels (20, 22) that are contiguous throughout the length of the housing. All three bore elements, the bore in the base (12) and the two retention ring housing bores (20, 22) will be of substantially the same diameter and circumference which is dictated by size of the diameter and circumference of the feeding tube to which the retention device (2) is applied.

As is also evident from FIG. 1, the first retention ring housing (6) is positioned on the top surface (10) of said base (4). Preferably, the axis of its centrally located bore (20) is substantially parallel with the longer, latitudinal x-axis of the oval base. This retention ring housing (6) is preferably split and is preferably comprised of two rings or fingers (or hooks) (6a, 6b) that are pliable and can be pulled apart for easier insertion of the tube. Such rings or fingers are preferably opposite facing. This retention ring housing (6) serves more as a guide than an attachment for the tube.

In another embodiment, the first retention ring housing (6) maybe substantially non-pliable or fixed, such as a short tube. In yet another embodiment the retention ring housing (6) may be of one or more pliable, deformable rings or fingers (6) which may be adjacent to or separated from each other.

The second retention ring housing (8) is positioned on the top surface (10) of the base (4) such that the axis of its centrally disposed bore (22) is out of axial alignment with the first retention ring bore (20). In a preferred embodiment, the second bore at least 15° out of alignment and most preferably is substantially perpendicular to the axis of the bore (20) of the first retention ring (6). This second retention ring may be tube-like or may optionally be configured with the pliable ring feature preferred in the first ring. Finally, one or more suture holes (24) is preferably disposed on one or both sides of said base (4) and these extend through the width of said base (4). These are utilized as one means to physically secure the feeding tube retention device to the body of the patient.

Figure 2:
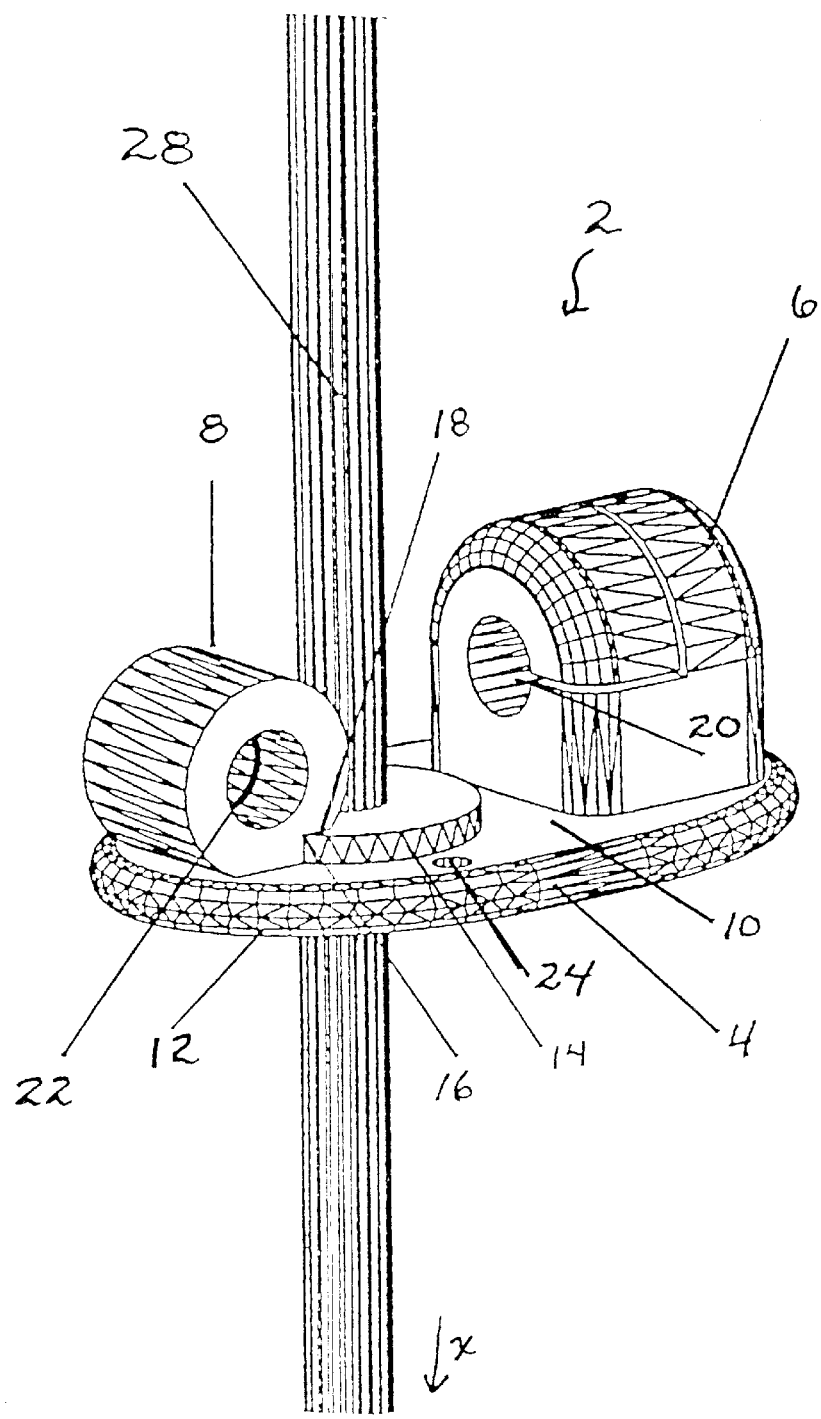
FIG. 2 is an overall schematic view of the feeding tube retention device of the present invention with the feeding tube threaded through the bore of the central base only.
Figure 3:
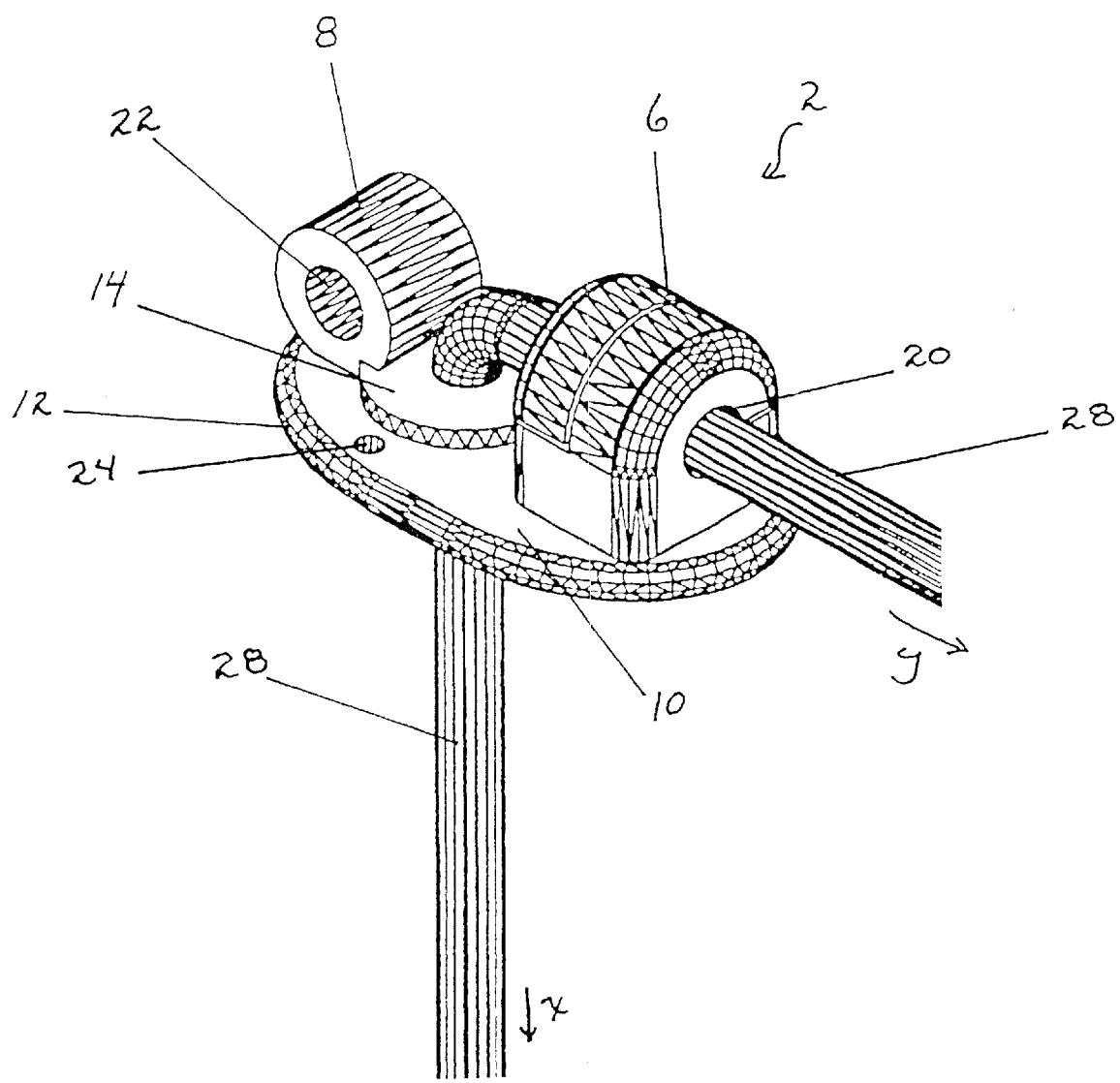
FIG. 3 is an overall schematic view of the feeding tube retention device showing the feeding tube threaded through both the central base bore and the bore of the first substantially cylindrical retention ring housing.
Figure 4:
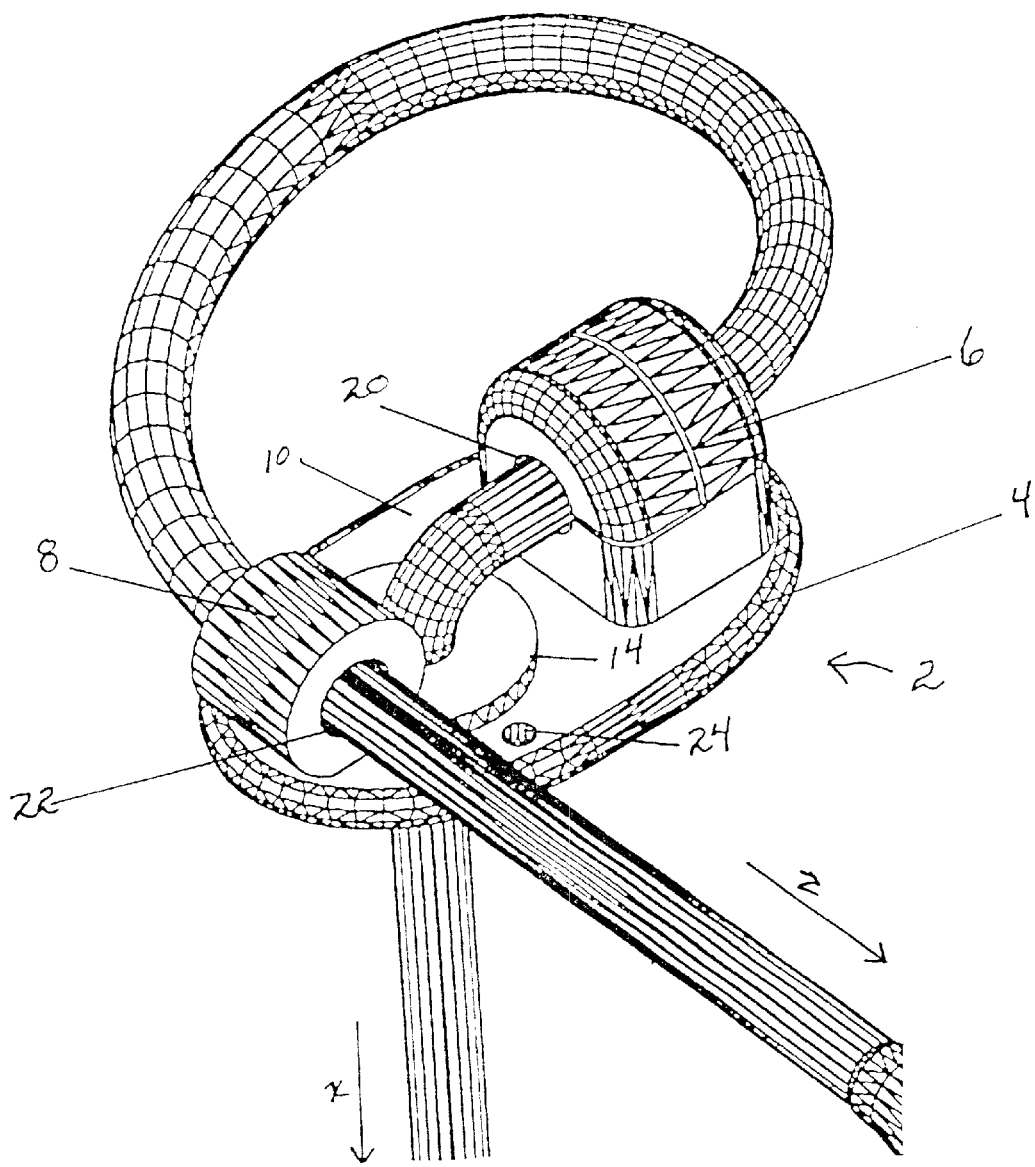
FIG. 4 is an overall schematic view of the feeding tube retention device showing the tube fully threaded through all three bores for maximum protection against traction.

Referring now to FIGS. 2, 3, and 4, the feeding tube retention device is shown in conjunction with a feeding tube (28) in order to better demonstrate how the tube is threadably attached to and removable from the retention device. The gastrostomy or jejunal feeding tube (28) exiting a patient's body (i.e. from below the base (4); arrow x), is first passed through the centrally disposed bore (12) of the substantially elevated disk element (14) as shown in FIG. 2. The feeding tube is then curved at approximately a ninety degree (90°) angle, preferably on a plane perpendicular to the base (4), and is threaded through the central bore (20) of the first retention ring housing (6) as is shown in FIG. 3. The feeding tube is then looped around at almost 270°, preferably on a plane parallel to the base so as to be threadably insertable in the central bore (22) of the smaller, second retention ring housing (8) whose axis is perpendicular to that of the bore (20) of the first retention housing. Of course, the tube could be bent by less than 270°, i.e., approaching 195° or even 180°, should the second retention ring housing (8) be more axially aligned to the first retention ring housing (6). The feeding tube itself then may lead to a Y-port connector (arrow z) which attaches to the nutritional or medicinal formula source.

Once the feeding tube is fed through the base (4) and retention ring housings as described above, the base (4) is attached to the skin of the patient using any one of a number of attachment means or methods known in the art such as sutures, staples, adhesive tapes or liquid adhesives. FIG. 4 shows the retention device fully engaged with a feeding tube containing a Y-port connector that engages the source of nutritional formula or medicine.

It is recognized that minor changes and alterations may be made to the design and structure of the retention device as described herein. However, to the extent any such changes do not materially alter the structure and function of the retention device herein described so as to operate in a substantially different manner, it is to be understood that any such changes are to be deemed as falling within the spirit and scope of the invention as set forth by the following claims.

What we claim is:

1. A catheter retention device comprising:

1) a base element having a bore passing through said base element;
2) a first retention ring adjacent to the bore for receiving a feeding tube from the base element, said first retention ring having a first retention ring bore and;
3) a second retention ring having a second retention ring bore and an axis, wherein said axis is out of alignment to said first retention ring bore.

2. The catheter retention device of claim 1 wherein said axis of said second retention ring bore is substantially perpendicular to said first retention ring bore.

3. The catheter retention device of claim 1 wherein the circumferences of said bore passing through said base element, said first retention ring bore and said second retention ring bore are substantially the same circumference as the outer perimeter of said feeding tube.

4. The catheter retention device of claim 3 wherein said first retention ring is comprised of a plurality of pliable rings.

5. The catheter retention device of claim 4 wherein said base element is substantially oval.

6. The catheter retention device of claim 5 wherein said bore in the base element and the first retention ring are situated to accommodate the feeding tube which has been bent approximately ninety degrees and is threadably insertable therethrough.

7. The catheter retention device of claim 6 configured to accept said feeding tube into the said second retention ring bore from said first retention ring bore, said feeding tube bent at approximately 270°.

8. The catheter retention device of claim 7 wherein said base element further comprises at least one suture hole.

9. The catheter retention device of claim 8 molded as a single unit from a material that includes at least one of a silicone rubber, thermoplastic rubber, polyvinyl chloride, and polyurethane.

10. The catheter retention device of claim 7 wherein said base element, said first retention ring and said second retention ring are molded separately from a material that includes at least one of a silicone rubber, thermoplastic rubber, polyvinylchloride, and polyurethane.

11. The catheter retention device of claim 11 wherein said feeding tube is one of a gastrostomy feeding tube or a jejunal feeding tube.

12. A method for the securing a catheter to a patient comprising the step of passing a catheter through a device comprising:
1) a base element having a bore passing through said base element;
2) a first retention ring having a first retention ring bore positioned at an end of said base element adjacent to said bore of said base element and;
3) a second retention ring having a second retention ring bore, wherein second retention ring bore has an axis substantially perpendicular to said first retention ring.

13. The method of claim 12 further comprising the steps of
1) inserting a distal end of a portion of said catheter exiting a patient's body through said bore of said base element;
2) bending said portion exiting said bore of said base element;
3) inserting said distal end through said first retention ring bore; and
4) bending a suitable length of said catheter exiting said first retention ring bore so as to be insertable in said second retention ring bore.

14. The method of claim 12 wherein said retention device is attached to said body by suturing.

15. The method of claim 14 wherein said catheter is one of a gastrostomy feeding tube or a jejunal feeding tube.

16. The catheter retention device of claim 1 further comprising an elevated disk element located on a surface of said base element.

17. The catheter retention device of claim 16 wherein said surface of said base element is the top surface.

18. The catheter retention device of claim 1 wherein said base element has a thickness less than or equal to 1.0 cm.

19. The catheter retention device of claim 18, wherein said thickness is from about 0.1 cm to about 0.5 cm.

* * * * *

UNITED STATES PATENT AND TRADEMARK OFFICE
CERTIFICATE OF CORRECTION

PATENT NO. : 6,471,676 B1  Page 1 of 1
DATED : October 29, 2002
INVENTOR(S) : Delegge et al.

It is certified that error appears in the above-identified patent and that said Letters Patent is hereby corrected as shown below:

Title page,
Item [56], References Cited, add new section:
-- OTHER PUBLICATIONS
Fontana R J, et al., "Jejunostomy Tube Placement in Refractory Diabetic Gastroparesis: A Retrospective Review", Am J of Gastroenterology, Vol. 91, No. 10, pp. 2174-2178, (1996). --

Column 8,
Line 1, change "claim 11" to -- claim 10 --.

Signed and Sealed this

Twenty-fourth Day of June, 2003

JAMES E. ROGAN
*Director of the United States Patent and Trademark Office*